US 6,685,742 B1

(12) United States Patent  
Jackson

(10) Patent No.: US 6,685,742 B1
(45) Date of Patent: Feb. 3, 2004

(54) ARTICULATED ANTERIOR EXPANDABLE SPINAL FUSION CAGE SYSTEM

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 0 days.

(21) Appl. No.: 10/292,723

(22) Filed: Nov. 12, 2002

(51) Int. Cl.$^7$ ................................................. A61F 2/44
(52) U.S. Cl. ................................................. 623/17.11
(58) Field of Search .......................... 623/17.11, 17.12, 623/17.13, 17.14, 17.15, 17.16; 606/61, 63; 411/24, 25, 32, 55, 71

(56) References Cited

U.S. PATENT DOCUMENTS

| 4,013,071 | A |   | 3/1977 | Rosenberg |
| 4,863,476 | A |   | 9/1989 | Shepperd |
| 5,015,255 | A |   | 5/1991 | Kuslich |
| 5,055,104 | A |   | 10/1991 | Ray |
| 5,059,193 | A |   | 10/1991 | Kuslich |
| 5,258,031 | A | * | 11/1993 | Salib et al. ................. 623/17 |
| 5,263,953 | A |   | 11/1993 | Bagby |
| 5,458,638 | A |   | 10/1995 | Kuslich et al. |
| 5,489,307 | A |   | 2/1996 | Kuslich et al. |
| 5,489,308 | A |   | 2/1996 | Kuslich et al. |
| 5,554,191 | A |   | 9/1996 | Lahille et al. |
| 5,593,409 | A |   | 1/1997 | Michelson |
| 5,609,636 | A |   | 3/1997 | Kohrs |
| 5,653,763 | A |   | 8/1997 | Errico et al. |
| 5,658,336 | A |   | 8/1997 | Pisharodi |
| 5,658,337 | A |   | 8/1997 | Kohrs et al. |
| 5,665,122 | A |   | 9/1997 | Kambin |
| 5,669,909 | A |   | 9/1997 | Zdeblick et al. |
| 5,683,391 | A |   | 11/1997 | Boyd |
| 5,693,100 | A |   | 12/1997 | Pisharodi |
| 5,702,453 | A |   | 12/1997 | Rabbe et al. |
| 5,776,197 | A |   | 7/1998 | Rabbe et al. |
| 5,776,198 | A |   | 7/1998 | Rabbe et al. |
| 5,782,832 | A |   | 7/1998 | Larsen et al. |
| 5,782,919 | A |   | 7/1998 | Zdeblick et al. |
| 5,797,909 | A |   | 8/1998 | Michelson |
| 5,865,847 | A |   | 2/1999 | Kohrs et al. |
| 5,885,287 | A |   | 3/1999 | Bagby |
| 5,893,889 | A | * | 4/1999 | Harrington ................. 623/17 |
| 5,980,522 | A |   | 11/1999 | Koros et al. |
| 6,039,761 | A | * | 3/2000 | Li et al. ................. 623/17 |
| 6,071,310 | A | * | 6/2000 | Picha et al. ................. 623/17 |
| 6,080,193 | A |   | 6/2000 | Hochshuler et al. |
| 6,102,950 | A |   | 8/2000 | Vaccaro |
| 6,117,174 | A |   | 9/2000 | Nolan |
| 6,129,763 | A |   | 10/2000 | Chauvin et al. |
| 6,159,244 | A |   | 12/2000 | Suddaby |
| 6,159,245 | A |   | 12/2000 | Meriwether et al. |
| 6,165,219 | A |   | 12/2000 | Kohrs et al. |
| 6,176,882 | B1 |   | 1/2001 | Biedermann et al. |
| 6,179,875 | B1 |   | 1/2001 | Von Stremple |
| 6,183,517 | B1 |   | 2/2001 | Suddaby |
| 6,190,414 | B1 | * | 2/2001 | Young et al. ............. 623/17.15 |
| 6,193,757 | B1 |   | 2/2001 | Foley et al. |
| 6,231,609 | B1 |   | 5/2001 | Mehdizadeh |
| 6,332,895 | B1 |   | 12/2001 | Suddaby |
| 6,443,989 | B1 | * | 9/2002 | Jackson ................. 623/17.15 |
| 6,454,807 | B1 |   | 9/2002 | Jackson |
| 6,491,724 | B1 | * | 12/2002 | Ferree ................. 623/17.11 |
| 2002/0128716 | A1 | * | 9/2002 | Cohen et al. ............. 623/17.15 |
| 2003/0065396 | A1 | * | 4/2003 | Michelson ............... 623/17.15 |

FOREIGN PATENT DOCUMENTS

WO      WO 97/00054     *  1/1997   ............. A61F/2/44

* cited by examiner

Primary Examiner—Eduardo C. Robert
Assistant Examiner—David C. Comstock
(74) Attorney, Agent, or Firm—Marcia J. Rodgers; Shughart Thomson & Kilroy, P.C.

(57) ABSTRACT

An articulated modular spinal fusion cage is implanted in the intervertebral space and adjusted in situ from an anterior access position to support adjacent vertebrae in normal curved alignment. The cage includes a first leg having a cylindrical pivot member and a second leg having a socket. The socket permits pivotal movement of the first leg with respect to the second leg to an anteriorly open, wedge-shaped orientation which may be selectively angularly adjusted. The laterally elongated socket and pivot member form a fulcrum that is positioned anteriorly from the posterior leg ends to enhance torsional stability and increase anterior preload. A driver is inserted through a bore in the socket and corresponding groove in the flange and is operable to engage a sloped interior surface of the first leg and to urge the anterior end upwardly by rotating the pivot member within the socket.

15 Claims, 2 Drawing Sheets

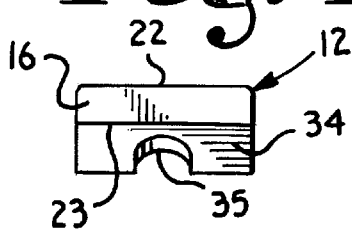
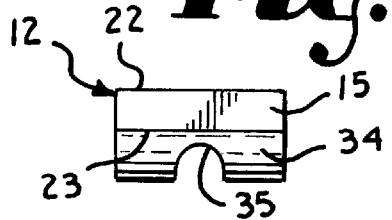
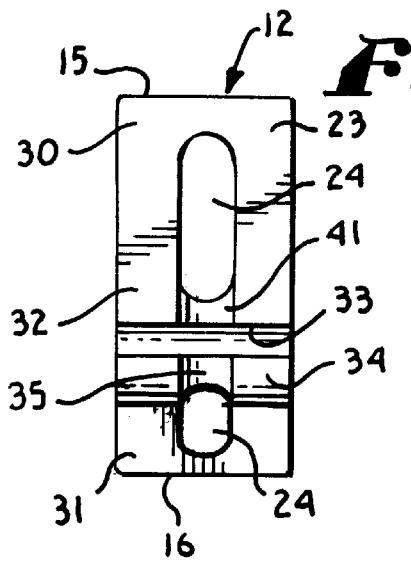
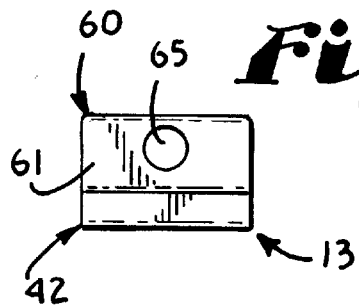
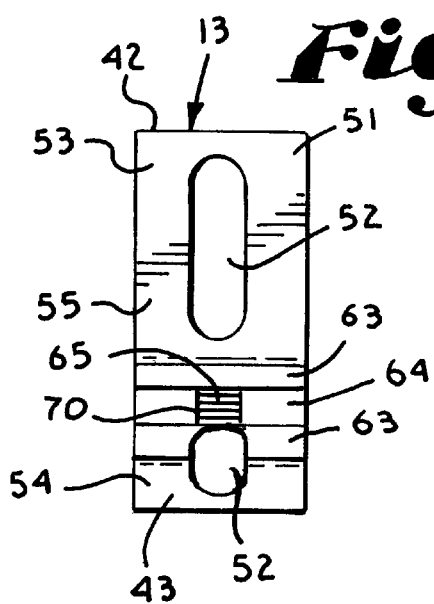

ARTICULATED ANTERIOR EXPANDABLE SPINAL FUSION CAGE SYSTEM

BACKGROUND OF THE INVENTION

The present invention is broadly concerned with a spinal fusion cage system. More particularly, it is directed to an articulated implant which can be installed between a pair of adjacent vertebrae and selectively expanded in situ to form a wedge with an adjustable angle of inclination for supporting and stabilizing the vertebrae in normal curved alignment in order to promote fusion of the aligned vertebrae.

The spine is a column of stacked vertebrae which are normally axially aligned along the median plane. When viewed from the front or back, the spine appears to be straight. When viewed from a lateral perspective, however, it is shown to be comprised of four distinct curves. Each vertebra is angularly displaced in the coronal plane in accordance with its position along one of the respective curves.

The structure of each vertebra includes a rounded, weight bearing anterior element, or vertebral body, which is separated from the adjacent superior and inferior vertebral bodies and cushioned by fibrocartilage pads or discs. These intervertebral discs support the adjacent vertebrae in an appropriate angular orientation within a respective spinal curve and impart flexibility to the spine so that it can flex and bend yet return to its original compound curvate configuration.

Aging, injury or disease may cause damage to the discs or to the vertebrae themselves. When this occurs, it may be necessary to surgically remove a disc and fuse the adjacent vertebral bodies into a single unit. Such surgical arthrodesis is generally accomplished by implanting a cage-like device in the intervertebral or disc space. The cages are apertured, and include a hollow interior chamber which is packed with live bone chips, one or more gene therapy products, such as bone morphogenic protein, cells that have undergone transduction to produce such a protein, or other suitable bone substitute material. Following implantation, bone from the adjacent vertebrae above and below the cage eventually grows through the apertures, fusing with the bone of the adjacent vertebral bodies and fixing the adjacent vertebrae as well as the cage in position.

Once the disc has been removed from the intervertebral space, the angular orientation of the adjacent vertebrae is established and stabilized by the three dimensional geometry of the implanted fusion cage, and the vertebrae will eventually fuse in this orientation. The lumbar curve presents a region of normal anterior convexity and posterior concavity or lordosis. There is a need for an anterior implant for use in this region which can be adjusted in situ to achieve and maintain normal lordosis of the vertebrae.

Previous attempts to achieve normal spinal curvature with fusion cages have involved trial insertion of cages of various different sizes into the intervertebral space. The cage is repeatedly removed and replaced with another unit of a slightly different size until an optimal angular incline is achieved. There is a need for a modular and articulated implant which can be installed in a first configuration, and adjusted in situ into a wedge configuration from an anterior access position.

Once installed in an intervertebral space, spinal implants are subject to compressive forces exerted by gravity and movement of the spinal column. Normal forward bending activity exerts substantially greater compressive force on the vertebrae than backward bending. Consequently, there is a need for an implant which will accept an increased anterior preload to withstand anterior compressive forces and to maintain the disc space height.

Spinal implants are also subject to twisting forces caused by unequal lateral distribution of weight on the adjacent vertebral bodies. This may occur, for example, during normal sideward bending and reaching activity. There is also a need for an implant which will provide torsional stability to resist such twisting forces. In particular, in order to withstand the greater compressive forces associated with forward bending movements, there is a need for an implant that will provide enhanced anterior torsional stability.

The apparatus of the present invention is specifically designed to provide a modular intervertebral implant which can be both installed and selectively expanded in situ from an anterior access position to form a wedge which stabilizes the adjacent vertebrae in normal curved alignment while providing lateral stability, increased anterior preload and enhanced anterior torsional stability.

SUMMARY OF THE INVENTION

The present invention is directed to an articulated modular cage system for implantation in the intervertebral space and adjustment in situ from an anterior access position to support the adjacent vertebrae in a normal curved alignment while permitting fusion of the adjacent bones. The fusion cage system of the present invention includes a first leg having a pivot member, a second leg having a socket for receiving the pivot member and a driver. The socket permits movement of the first leg about an axis of pivotal rotation from a closed, parallel insertion position to an anteriorly open, wedge-shaped orientation which may be selectively adjusted to provide appropriate angular support. The socket and pivot member are laterally elongated to provide lateral support. The pivot member includes a cylindrical notch or aperture, and the socket includes a threaded bore which are aligned for receiving a driver.

The driver is operable to engage a sloped interior surface of the first leg and to urge the anterior end of the first leg apart from the anterior end of the second leg while causing the pivot member to rotate within the socket. Registry of the driver within both the bore and the aperture serves to prevent lateral displacement of the pivot member within the socket. The pivot member and socket are inset or positioned anteriorly of the posterior ends of the respective legs in order to enhance torsional stability and to optimize the anterior preload. This is achieved by decreasing a moment arm length between an effective area of engagement of the adjacent vertebrae and the location of the connection between the legs of the cage. Positioning the pivot axis anterior of the posterior ends of the legs also helps to optimize the intervertebral spacing and angular alignment of the adjacent vertebrae to avoid undesirably stressing the next vertebrae beyond the vertebrae engaged by the fusion cage.

Objects and advantages of this invention will become apparent from the following description taken in conjunction with the accompanying drawings wherein are set forth, by way of illustration and example, certain embodiments of the invention.

BRIEF DESCRIPTION OF THE DRAWINGS

FIG. 4 is a front elevational view taken along line 4—4 of FIG. 3 showing an anterior end of the top leg with the driver omitted.

FIG. 5 is a rear elevational view taken along line 5—5 of FIG. 3 showing a posterior end of the top leg with the driver omitted.

FIG. 6 is a bottom plan view taken along line 6—6 of FIG. 2, showing a bottom side of the top leg of the cage with the driver omitted.

FIG. 7 is a front elevational view taken along line 7—7 of FIG. 3 showing an anterior end of the bottom leg with the driver omitted.

FIG. 8 is a top plan view taken along line 8—8 of FIG. 2 showing a top side view of the bottom leg with the driver omitted.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and is not intended to be limiting. For example, the words "anterior", "posterior", "superior" and "inferior" and "lateral" and their derivatives will refer to the device as it may be installed in anatomical position as depicted in FIGS. 2–3.

Figure 1:
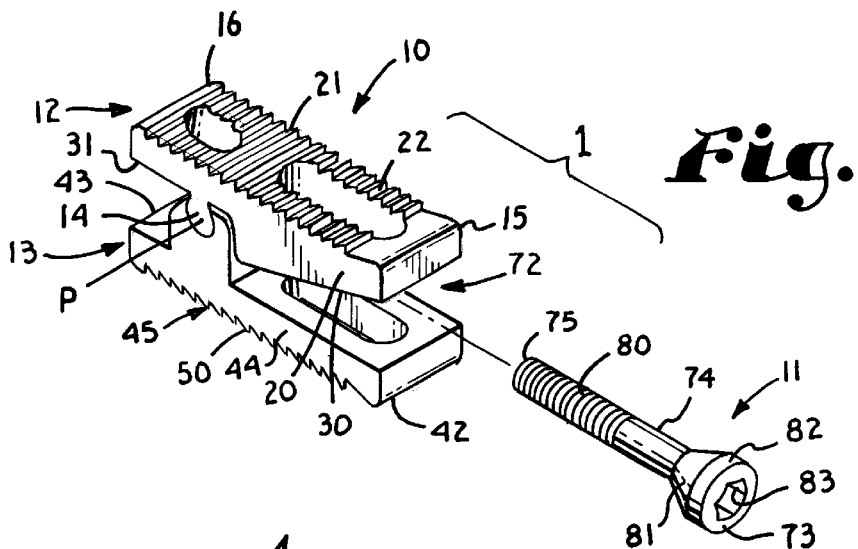
FIG. 1 is a partially exploded perspective view of an articulated expandable spinal fusion cage system in accordance with the present invention, illustrating a threaded driver.
Figure 2:
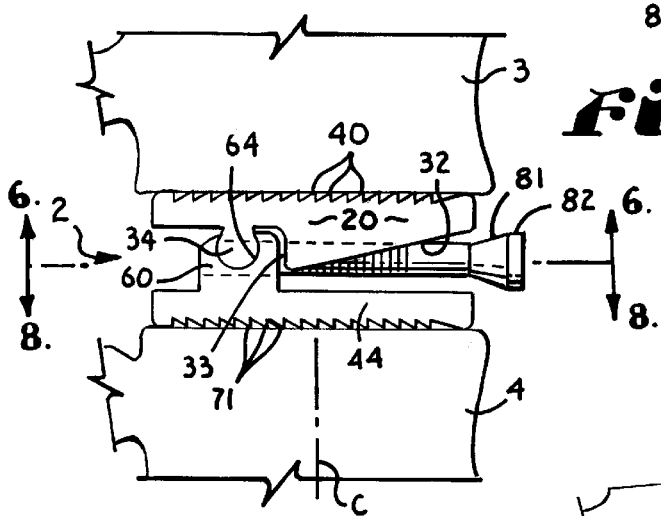
FIG. 2 is a fragmentary side elevational view of the cage of FIG. 1 installed between adjacent vertebrae, showing a bore and interior surfaces in phantom to illustrate the path of installation of the driver.
Figure 3:
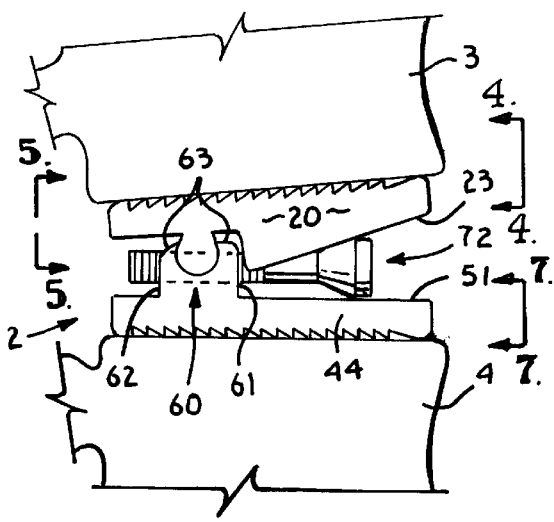
FIG. 3 is a view similar to FIG. 2, illustrating the driver installed between the bearing surfaces of the legs and the anterior portions of adjacent vertebrae displaced to achieve lordosis.

Referring now to the drawings, an articulated anterior expandable spinal fusion cage system in accordance with the invention is generally indicated by the reference numeral 1 and is depicted in FIGS. 1–8. FIGS. 2 and 3 illustrate a partial side view of a human spine showing an intervertebral region 2, which is the functional location of implantation of the fusion cage system 1, between the vertebral bodies of selected upper and lower adjacent vertebrae 3 and 4.

Referring again to FIG. 1, the fusion cage system 1 broadly includes a fusion cage 10 and a driver 11. The cage 10 includes a first leg 12 depicted and normally installed in a superior orientation and adjustably coupled with a second, normally inferior leg 13 by a pivot joint or bearing 14 positioned posteriorly of a centerline C, passing midway between the ends. The first leg 12 has an anterior end 15, a posterior end 16 and a pair of opposed sides 20 interconnected by a central web portion 21. The sides of the cage 20 are depicted as generally planar and orthogonal to the web portion 21, although they may also be of curvate, angular or compound curvate or angular construction. The legs 12 and 13 are normally of the same width and length, but it is also foreseen that either of the legs 12 and 13 may be of somewhat broader construction in order to selectively enhance the superior or inferior bone-supporting surface area.

The first leg 12 includes an outer, bone-supporting surface 22 and an inner surface 23, best shown in FIG. 6. The web 21 is apertured by one or more ports or windows 24, which extend between the outer and inner surfaces 22 and 23.

The leg inner surface 23 includes an anterior portion 30 and a posterior portion 31. The anterior portion 30 has a linear cam or bearing surface 32 that terminates posteriorly in a first abutment surface or stop 33 that is generally orthogonal to the outer surface 22. When viewed from the side (FIGS. 1–3), the bearing surface 32 slopes downwardly at an angle as it approaches the second end 16 in the configuration of a ramp or wedge having the abutment surface 33 as its base. The posterior portion 31 extends in generally parallel relationship with the web outer surface 22 except for a dependent, generally cylindrical pivot member 34 having a pivot axis P. The pivot member 34 depends the entire width of the cage 10 between the sides 20 and includes a central notch, aperture or groove 35 (FIGS. 4–6) for receiving the driver 11.

The leg outer surface 22 includes a series of serrations or teeth 40 for engaging the surface of a respective adjacent vertebra 3 against slippage along an anterior-posterior axis within the intervertebral joint 2. The leg inner surface 23 is generally smooth. The anterior bearing surface 32 is axially grooved to form a channel 41 (FIG. 6) adapted for sliding reception of the driver 11.

The second leg 13 has an anterior first end 42, a posterior second end 43 and a pair of opposed sides 44 interconnected by a central web portion 45. The leg 13 also includes an outer, bone-supporting surface 50 and an inner surface 51, best shown in FIG. 8. The web 45 is apertured by one or more ports or windows 52, which extend between the outer and inner surfaces 50 and 51.

The leg inner surface 51 includes an anterior portion 53 and a posterior portion 54. The anterior portion 53 has a support surface 55 that extends in generally parallel relationship with the leg outer surface 50. The posterior portion 54 also extends in generally parallel relationship with the leg outer surface 50, except for an upstanding, approximately rectangular knuckle 60. The knuckle 60 is elongated laterally, so that it extends the full width of the cage 10 between the sides 44.

The knuckle 60 includes anterior, posterior, and upper or superior surfaces 61, 62 and 63 (FIG. 3). The superior surface 63 includes a laterally extending, generally cylindrical channel which serves as a socket 64 for receiving the cylindrical pivot member 34 of the first leg 12 in pivoting relationship to form the pivot bearing 14. The laterally elongated pivot member 34 and socket 64 cooperatively provide lateral support to the cage 10 against sideward bending stresses which may be brought to bear following installation.

The anterior and posterior knuckle surfaces 61 and 62 are generally orthogonal to the outer surface 50, and the anterior surface 61 serves as an abutment surface or stop for the first leg abutment surface 33. The upper knuckle surface 63 is generally parallel with the outer surface 50, except that the posterior aspect is somewhat relieved so that it does not serve as a stop when the first leg 12 pivots in the socket 64 of the second leg 13. As shown in FIGS. 7 and 8, the knuckle 60 includes a central bore 65 having flighting or threads 70 for receiving and engaging the driver 11.

Like the first leg 12, the second leg outer surface 50 includes a series of bone-engaging serrations or teeth 71

(FIG. 2). The leg inner surface 51 is generally smooth. The first and second leg anterior portions 15 and 42 cooperatively define an open-sided chamber 72 when the cage 10 is assembled as depicted in FIGS. 1–3.

The driver 11 is depicted in FIG. 1 to include a radially expanded head 73 and a shaft 74 terminating in a generally flattened driving end 75. The shaft 74 is sized and shaped for reception within channel 41, and preferably includes threads 80 for operable reception within matingly threaded bore 65, with the radially expanded driver head 73 engaging the angled bearing surface 32 of the upper leg 12. It is also foreseen that in certain applications the shaft 74 could be smooth and unthreaded. The driver head 73 is coupled with the shaft 74 by a generally frustoconical shank portion 81, and terminates in a narrow, generally cylindrical bearing surface 82. The head 73 also includes a non-round socket or receiver 83 configured for non-slip reception of a driving tool such as a wrench (not shown). While the receiver 83 is depicted as being generally hexagonal in shape, it is understood that it may be configured as a square, slot, multilobular or any other shape corresponding to a preselected driving tool.

The diameter of the driver head 73 and the length of the shaft 74 are sized so that the driver 11 extends posteriorly through the channel 41 of the upper leg 12 for driving registry of the shaft 74 within the groove 35 of the first leg and central bore 65 of the lower leg 13 and engagement of the driver head bearing surface 82 with the angled bearing surface 32 of the upper leg 12. In this manner, the channel 41, groove 35 and bore 65 cooperate with the shaft 74 of the driver 11 to effectively lock the legs 12 and 13 against lateral displacement.

The legs 12 and 13 and driver 11 may be constructed of a non-metallic material such as carbon fiber reinforced composite or tissue-derived polymer material, or of a strong, inert material having a modulus of elasticity such as a metal, like stainless steel or titanium alloy, or of porous tantalum or any other biocompatible material or combination of materials. It is foreseen that it may be desirable in certain applications to employ a radiolucent material such as carbon fiber reinforced composite which will not block post operative radiographic images of bridging bone growth.

It is also foreseen that the fusion cage system 1 may also include a pair of independently adjustable cages 10, installed in generally side-by-side relationship within a single intervertebral space 2, as set forth more fully in U.S. Pat. No. 6,454,807 and incorporated herein by reference.

In use, the anterior surface of a selected intervertebral region 2 of the spine of a patient is surgically exposed. The soft tissues are separated, the disc space is distracted and the disc is removed, along with any bone spurs which may be present. The disc space is distracted to a predetermined height which serves to decompress any affected nerve roots and to permit preparation of the intervertebral region 2.

The fusion cage system 1 is assembled by a surgeon or assistant by laterally aligning the cylindrical pivot member 34 of the first leg 12 with the socket 64 of the second leg 13 and sliding the pivot member 34 laterally into engagement with the socket 64 until the groove 35 is aligned with the bore 65. The driver 11 is next grasped and the threaded end 75 is introduced into the bore 65 and rotated by hand or with the use of an insertion tool until the threads 80 of the driver shaft 74 engage the threads 70 of the bore 65. Registry of the driver 11 within both the groove 35 of the first leg 12 and the bore 65 of the second leg serves to prevent any lateral movement or play of the pivot member 34 within the socket 64. The driver 11 may be rotated a few additional turns in order to secure against disengagement from the bore 65 during insertion. However, unless the intervertebral space 2 is substantially larger than the cage 10, rotation is generally stopped when the conical shank 81 engages the bearing surface 32 of the first leg 12, so that the cage 10 can be inserted in its smallest, or closed configuration.

The first and second leg anterior first ends 15 and 42 are next grasped and pressed together until the first leg abutment surface 33 comes to rest against the second leg abutment surface or stop 61 and the cage 10 is maximally compressed. The assembled fusion cage 10 presents a closed, overall rectangular configuration, with the outer surfaces 22 and 50 of the legs 12 and 13 in a generally parallel orientation, as depicted in FIGS. 1 and 2 and the driver 11 projecting slightly anteriorly from the cage 10.

The cage 10 may be press-fit directly into the distracted intervertebral region 2, or the vertebrae 3 and 4 may be predrilled to receive the cage system 1. Although an anterior approach is preferred, it is foreseen that a posterior or even lateral approach could also be employed.

The surgeon next positions a tool (not shown) in the driver head 73 and rotates the tool in a clockwise or posteriorly advancing direction to drive or pull the threaded shaft 74 further into the bore 52 and advance the head 73 in a posterior direction. Continued rotation of the driver 11 simultaneously causes the end 75 to advance posteriorly, the pivot member 34 to rotate within the socket 64, and the bearing surface 32 of the first leg 12 to ride up over the beveled shank 81 until the bearing surface 82 of the driver 11 engages the bearing surface 32 of the first leg 12. In this manner, rotational advancement of the driver 11 causes it to progressively wedge the bearing surface 32 apart from the support surface 55 of the second leg 13 until the cage 10 begins to assume a generally wedge shape when viewed from the side.

In this manner, the angle formed by the outer, bone supporting surfaces 22 and 50 of the legs 12 and 13, is determined by the displacement of the bearing surfaces 32 of the first leg 12 away from the support surface 55 of the second leg 13, which in turn is determined by the posterior advancement of the driver bearing surface 82 along the first leg bearing surface 32. The driver 11 is of a preselected size to cause displacement of the first leg 12 to form the cage 10 into an appropriate wedge shape which will support the adjacent vertebrae 3 and 4 at the proper height as well as the desired angular alignment to achieve normal curvature of the respective spinal region.

Advantageously, the laterally elongate cylindrical configuration and anteriorly inset or forward positioning of the pivot bearing 14 cooperatively formed by the pivot member 34 and socket 64, relative to the posterior ends 16 and 43 of the legs 12 and 13, enhance both the lateral and torsional stability of the cage system 1 as well as its anterior-preload. The configuration of the channel 41 for receiving the driver shaft 74 and the anterior preload also cooperate to enhance torsional stability.

The surgeon next transplants a quantity of packed bone cells or a suitable bone substitute material into the chamber 72 by a lateral approach through the open area between the first and second legs 12 and 13. Alternatively, the bone cells may be introduced into the chamber 72 by a posterior approach through the bore 65 prior to installation of the driver 11 or by any combination of these methods. Bone for use in the graft may be harvested from the patient as live bone, from a bone bank or from a cadaver. Demineralized bone matrix, bone morphogenic protein or any other suitable material may also be employed.

Following implantation, the bone grows between vertebrae 3 and 4, through the windows 24 and 52 with the bone in the chamber 72 and around the cage system 1 to fuse the bodies of vertebrae 3 and 4 together.

Those skilled in the art will appreciate that the fusion cage 10 may also be assembled and installed into the intervertebral space 2 prior to insertion of the driver 11 into the bore 65. In addition, while a single exemplary driver 11 and cage 10 having a wedge-shaped first leg 12 is depicted, a variety of drivers 11 and cages 10, having variously configured bearing surfaces 32 of different shapes, each producing a different degree of displacement of the first leg 12 may be incorporated in a set to allow the surgeon to preselect a cage system 1 to achieve a desired angle of displacement and consequent positioning of the vertebrae 3, 4 relative to each other. It is foreseen that various other configurations of the pivot bearing 14 could be advantageously employed in the cage system 1.

The cage system 1 of the invention is designed to permit adjustment by rotation of the driver 11 in situ until the desired alignment between the vertebra 3 and 4 is achieved. However, if necessary, the cage system 1 may also be removed and the installation repeated using a cage 10 and driver 11 having different configurations until the desired angular alignment is achieved.

It is to be understood that while certain forms of the present invention have been illustrated and described herein, it is not to be limited to the specific forms or arrangement of parts described and shown.

What is claimed and desired to be secured by Letters Patent is as follows:

1. A spinal fusion cage apparatus for implanting between adjacent vertebrae and comprising:
   a) a fusion cage having a first leg and a second leg, each leg having a first end, a second end, and an outer support surface therebetween, said first ends being expandably coupled, said cage being implantable between adjacent vertebrae with said support surfaces of said legs engaging said vertebrae;
   b) an articulated pivot joint coupled with said legs and positioned in between said first and second leg ends; said pivot joint including a knuckle positioned on said second leg; said knuckle having an elongated cylindrical socket extending laterally thereof and a threaded driver bore formed therethrough; said pivot joint including a cylindrical pivot member extending laterally across said first leg and received in said cylindrical socket to pivotally connect said first and second legs, said pivot member having a notch formed therein which is generally aligned with said driver bore in said knuckle when said pivot member is received in said socket; and
   c) a driver adjustably engaged between said first and second legs and operable for urging said first ends apart and pivoting said first leg for moving said support surface of said first leg of said fusion cage to form a selected angle relative to said support surface of said second leg; said driver being threaded and being threadedly received in said driver bore; and said driver cooperation with said notch in said pivot member to prevent lateral displacement of said first leg and said second leg.

2. The apparatus according to claim 1, wherein:
   a) said first leg includes a sloped inner bearing surface;
   b) said driver includes a head; and
   c) said driver head engages said inner bearing surface as said driver advances within said bore urging said first ends apart.

3. The apparatus according to claim 1, wherein:
   a) said first and second outer support surfaces include ports for permitting bone cells to grow therethrough and fuse said adjacent vertebrae.

4. The apparatus according to claim 1, wherein:
   a) said first and second outer support surfaces include serrations.

5. The apparatus according to claim 1, wherein:
   a) said first leg includes a stop structure for abutting engagement with said second leg.

6. The apparatus according to claim 1, wherein said apparatus includes:
   a) a second fusion cage for implanting in side-by-side relationship with said fusion cage between a pair of adjacent vertebrae.

7. A spinal fusion cage apparatus for implanting between adjacent vertebrae and comprising:
   a) an inferior leg with an inferior support surface for supporting engagement with an inferior vertebra;
   b) a superior leg with a superior support surface for supporting engagement with a superior vertebra adjacent said inferior vertebra;
   c) said superior leg being pivotally connected to said inferior leg by a pivot joint having a lateral axis to form an articulated spinal fusion cage having a posterior end and an opposed anterior end;
   d) a threaded driver member adjustably engaged between said inferior leg and said superior leg to position said superior leg at a selected angle relative to said inferior leg;
   e) said pivot joint being inset a selected distance anteriorly from said posterior end of said cage to impart a selected spacing and relative angular relationship between said inferior and superior vertebrae;
   f) said pivot joint including a knuckle positioned on said inferior leg and extending toward said superior leg, said knuckle having an elongated cylindrical socket extending laterally thereof;
   g) said knuckle having a threaded bore formed therethrough and threadedly receiving said driver member;
   h) said pivot joint including a cylindrical pivot member extending laterally across said superior leg, said pivot member being received in said knuckle to pivotally connect said superior leg to said inferior leg;
   i) said pivot member having a notch formed therein to enable clearance by said driver member; and
   j) said notch in said pivot member cooperating with said driver member to prevent relative lateral displacement of said superior leg and said inferior leg.

8. The apparatus according to claim 7, wherein:
   a) said superior leg includes a sloped inferior bearing surface;
   b) said driver member includes a head; and
   c) said driver member head engages said sloped inferior bearing surface to position said superior leg at a selected angle relative to said inferior leg.

9. The apparatus according to claim 8, wherein:
   a) said sloped inferior bearing surface includes a groove for receiving said driver member.

10. The apparatus according to claim 7, wherein:
    a) said inferior and superior support surfaces include ports for permitting bone cells to grow therethrough and fuse said inferior and superior vertebrae.

11. The apparatus according to claim 7, wherein:
    a) said inferior and superior support surfaces each include serrations for preventing disengagement of said spinal fusion cage from said inferior and superior vertebrae.

12. The apparatus according to claim 7, wherein:
    a) said superior leg includes a stop structure for abutting engagement with said inferior leg.

13. In a spinal fusion cage apparatus for implanting between adjacent vertebrae including a fusion cage having a first leg, a second leg, and a driver, each leg having a first end, a second end, and an outer support surface therebetween, said first ends being expandably coupled, said cage being implantable between adjacent vertebrae with said support surfaces of said legs engaging said vertebrae, said legs cooperatively forming a pivot joint, said driver received between said legs and operable for urging said first ends apart for moving said first support surface of said fusion cage to form a selected angle, the improvement comprising:
    a) said pivot joint being articulated and inset a selected distance from said second ends of said legs to impart a selected spacing and relative angular relationship between said adjacent vertebrae upon pivoting;
    b) said pivot joint including a knuckle positioned on said second leg; said knuckle having an elongated cylindrical socket extending laterally thereof and a threaded driver bore formed therethrough; said pivot joint including a cylindrical pivot member extending laterally across said first leg and received in said cylindrical socket to pivotally connect said first and second legs, said pivot member having a notch formed therein which is generally aligned with said driver bore in said knuckle when said pivot member is received in said socket; and
    c) said driver being a threaded driver which is adjustably engaged between said first and second legs; said driver being threadedly received in said driver bore; and said driver cooperating with said notch in said pivot member to prevent lateral displacement of said first leg and said second leg.

14. The apparatus according to claim 13, wherein:
    a) said first and second legs are connected only by said pivot joint.

15. A spinal fusion cage apparatus for implanting between adjacent vertebrae and comprising:
    a) an inferior leg including an inferior support surface for supporting engagement with an inferior vertebra, said inferior surface including a knuckle having a cylindrical socket formed therein and having a threaded bore formed therethrough;
    b) a superior leg including a superior support surface for supporting engagement with a superior vertebra adjacent said inferior vertebra, and including a cylindrical pivot member, and a sloped inferior bearing surface;
    c) said socket and said pivot member forming a pivot joint pivotally coupling said superior leg to said inferior leg to form an articulated spinal fusion cage having a posterior end and an opposed anterior end;
    d) said pivot member including a groove aligned with said bore when said pivot member is received within said socket;
    e) a threaded driver member threadedly received within said bore and said groove and having a head engaging said bearing surface to position said superior leg at a selected angle relative to said inferior leg, said driver member cooperating with said groove to prevent lateral displacement of said superior leg and said inferior leg; and
    f) said pivot joint being inset a selected distance anteriorly from said posterior end of said cage to impart a selected spacing and relative angular relationship between said inferior and superior vertebrae.

* * * * *

UNITED STATES PATENT AND TRADEMARK OFFICE
CERTIFICATE OF CORRECTION

PATENT NO.   : 6,685,742 B1
DATED        : March 25, 2004
INVENTOR(S)  : Roger P. Jackson It is certified that error appears in the above-identified patent and that said Letters Patent is hereby corrected as shown below:

Column 7,
Line 65, the word "cooperation" should be changed to read -- cooperating. --

Signed and Sealed this

Fifteenth Day of June, 2004

JON W. DUDAS
*Acting Director of the United States Patent and Trademark Office*